US005809801A

United States Patent [19]
Cates, Jr. et al.

[11] Patent Number: 5,809,801
[45] Date of Patent: Sep. 22, 1998

[54] CRYOGENIC ACCUMULATOR FOR SPIN-POLARIZED XENON-129

[75] Inventors: Gordon D. Cates, Jr., Skillman, N.J.; Bastiaan Driehuys, Bristol, Pa.; William Happer, Princeton, N.J.; Eli Miron, Princeton, N.J.; Brian Saam, Princeton, N.J.

[73] Assignee: The Trustees of Princeton University, Princeton, N.J.

[21] Appl. No.: 622,865

[22] Filed: Mar. 29, 1996

[51] Int. Cl.$^6$ .................................................. F25J 1/00
[52] U.S. Cl. ................................. 62/637; 62/919; 62/925
[58] Field of Search ............................. 62/637, 919, 925, 62/55.5, 3.1

[56] References Cited

U.S. PATENT DOCUMENTS

| | | | |
|---|---|---|---|
| 3,748,864 | 7/1973 | Lofredo et al. | 62/919 |
| 4,080,429 | 3/1978 | Koeppe et al. | 62/925 |
| 4,369,048 | 1/1983 | Pence | 62/925 |
| 4,417,909 | 11/1983 | Weltmer, Jr. | 62/925 |
| 4,599,462 | 7/1986 | Michl | 62/637 |
| 4,755,201 | 7/1988 | Eschwey | 62/55.5 |
| 4,977,749 | 12/1990 | Sercel | 62/55.5 |
| 5,007,243 | 4/1991 | Yamaguchi et al. | 62/55.5 |
| 5,039,500 | 8/1991 | Shino et al. | 62/925 |
| 5,161,382 | 11/1992 | Missimer | 62/55.5 |

OTHER PUBLICATIONS

Wagshul, et al., "Optical Pumping Of High–Density Rb With A Broadband Dye Laser And GaAlAs Siode Laser Arrays: Application to $^3$He Polarization", *Physical Review A*, vol. 40, No. 8, pp. 4447–4454 (1989).

Gatzke, et al., "Extaordinarily Slow Nuclear Spin Relaxation In Frozen Laser–Polarized $^{129}$Xe", *Physical Review Letters*, vol. 50, No. 5, pp. 690–693 (1993).

Cates, et al., "Laser Production Of Large Nuclear–Spin Polarization In Frozen Xenon", *Physical Review Letters*, vol. 65, No. 20, pp. 2591–2594 (1990).

Becker, et al., "Study Of Mechanical Compression Of Spin–Polarized $^3$He Gas", *Nuclear Instruments And Methods In Physics Research*, vol. A 346, pp. 45–51 (1994).

Middleton, et al., "MR Imaging With Hyperpolarized $^3$He Gas", *Magnetic Resonance In Medicine*, vol. 33, pp. 271–275 (1995).

Cummings, et al., "Optical Pumping of Rb Vapor Using High–Power $Ga_{2-x}Al_xAs$ Diode Laser Arrays", *Physical Review A*, vol. 52, No. 6, pp. 4842–4851 (1995).

Middleton, "The Spin Structure of The Neutron Determined Using A Polarized $^3$He Target", *Ph.D Dissertation,* Princeton University (1994).

*Primary Examiner*—Ronald C. Capossela
*Attorney, Agent, or Firm*—Hoffmann & Baron, LLP

[57] ABSTRACT

A method and apparatus for accumulation of hyperpolarized $^{129}$Xe is disclosed. The method and apparatus of the invention enable the continuous or episodic accumulation of flowing hyperpolarized $^{129}$Xe in frozen form. The method also permits the accumulation of hyperpolarized $^{129}$Xe to the substantial exclusion of other gases, thereby enabling the purification of hyperpolarized $^{129}$Xe. The invention further includes $^{129}$Xe accumulation means which is integrated with $^{129}$Xe hyper polarization means in a continuous or pulsed flow arrangement. The method and apparatus enable large scale production, storage, and usage of hyperpolarized $^{129}$Xe for numerous purposes, including imaging of human and animal subjects through magnetic resonance imaging (MRI) techniques.

41 Claims, 1 Drawing Sheet

CRYOGENIC ACCUMULATOR FOR SPIN-POLARIZED XENON-129

This invention was made with Government support under Grant Nos. DAAH04-94-G-0204, DAMD1794J4469, and F49620-94-0466. The Government may have rights in this invention.

BACKGROUND OF THE INVENTION

The invention relates to apparatus and methods for hyperpolarizing a noble gas. Specifically, the invention relates to methods and apparatus for manufacturing and accumulating significant quantities of a hyperpolarized noble gas in a continuous manner.

Nuclear magnetic resonance (NMR) is a phenomenon which can be induced through the application of energy against an atomic nucleus being held in a magnetic field. The nucleus, if it has a magnetic moment, can be aligned within an externally applied magnetic field. This alignment can then be transiently disturbed by application of a short burst of radio frequency energy to the system. The resulting disturbance of the nucleus manifests as a measurable resonance or wobble of the nucleus relative to the external field.

For any nucleus to interact with an external field, however, the nucleus must have a magnetic moment, i.e., non-zero spin. Experimental nuclear magnetic resonance techniques are, therefore, limited to study of those target samples which include a significant proportion of nuclei exhibiting non-zero spin. A highly preferred such nucleus is the proton ($^1H$), which is typically studied by observing and manipulating the behavior of water protons ($^1H_2O$) in magnetic fields. Other nuclei, including certain noble gas nuclei such as $^3He$ and $^{129}Xe$, are in principle suited to study via NMR. However, the low relative natural abundance of these isotopes, their small magnetic moments, and other physical factors have made NMR study of these nuclei difficult if not impossible to accomplish.

One important consideration in studying noble gas nuclei via NMR is that they normally yield only a very low NMR signal intensity. It is known, however, that the spin polarization of such noble gases as $^3He$ and $^{129}Xe$ can be increased over natural levels, i.e., populations of these isotopes can be artificially "hyperpolarized", to provide a much larger NMR signal. One preferred hyper polarization technique is known as spin exchange hyper polarization. Without describing this technique in exhaustive detail, in this scenario a noble gas is hyperpolarized via interaction with an alkali-metal vapor, such as rubidium, which itself has been polarized by absorption of laser energy of an appropriate wavelength. The polarized rubidium transfers its polarization to the noble gas through a phenomenon known as spin exchange transfer. The end result is that the noble gas becomes "hyperpolarized", i.e., more polarized than it would otherwise be. Details of the theory underlying the spin exchange hyper polarization technique are available in the literature.

While well established as a theoretical phenomenon, the actual practice of spin exchange hyper polarization has proven to be something of an art. The production and handling of hyperpolarized noble gases is not only logistically difficult, it is expensive as well. Moreover, due to the experimental nature of spin exchange studies, the production of hyperpolarized noble gases has typically been undertaken only on a small scale. Exquisite craftsmanship is typically required, involving expertise in a variety of fields including lasers, electronics, glass-blowing, ultra-high vacuum pump operation, high-purity gas handling, as well as nuclear magnetic resonance spectroscopy.

For example, the production of a single sample of hyperpolarized noble gas has typically involved the fabrication of a single-use sealed glass cell with a volume capacity of only a few tens to a few hundred cubic centimeters. Such cells have required delicacy in manufacture, yet their quality, as measured by their tendency to depolarize the noble gas, has not always been predictable. Moreover, use of such cells for spin exchange requires that they be sealed with the alkali metal present therein. This has meant that care must be taken to remove impurities which can cause oxidation of the metal and consequent ruination of the cell. Other problems arise in the glass itself which can depolarize the noble gas faster than it can be polarized. For study of polarized noble gas by NMR techniques, the sealed cell must be cracked open or destroyed to release the hyperpolarized gas into the NMR spectrometer. Proceeding to the next sample has required repeating all of these steps, including fabricating and filling a new glass cell, which might or might not have similar qualities, resulting in a tedious and often unpredictable procedure.

Middleton established for the first time the possibility of making sealed pumping cells capable of containing larger quantities of a noble gas for hyper polarization by the spin exchange technique. Middleton H., *The Spin Structure of the Neutron Determined Using a Polarized$^3He$ Target*, Ph.D. Dissertation, Princeton University (1994). Even so, the reliability of the procedures described in this publication have not proven to be suited to routine use, in that sample-to-sample variability has remained a problem. Moreover, there is no disclosure in this document of any method of making refillable cells or cells which could be used on a continuous or flowing basis without significant rehabilitation. Accordingly, while progress in cell manufacture has occurred, the art has not provided means for making refillable or continuous flow spin exchange pumping cells.

It has also been known that hyperpolarized $^{129}Xe$ can be frozen but yet retain a significant proportion of its polarization. Indeed, it is known that freezing $^{129}Xe$ can actually prolong the polarization lifetime beyond that which can normally be achieved by keeping the $^{129}Xe$ in a gaseous state. Accordingly, sealed glass cells containing small amounts of hyperpolarized $^{29}Xe$ have been frozen, stored, and later thawed (sublimed) for use. See, e.g., Cates et al., *Phys. Rev. Lett.* 65(20), 2591–2594 (1990). The Cates document projects that small amounts (up to about 1 g/hr) of $^{129}Xe$ could be accumulated, but provides no practical indication of how such a result might be achieved. This paper also fails to provide any indication of whether the accumulation of larger quantities of frozen $^{129}Xe$ would be possible.

Alternatively, a publication by Becker et al., *Nucl Inst. &Meth. in Phys. Res. A*, 346:45–51 (1994) describes a method for producing hyperpolarized $^3He$ by a distinctly different polarization method known as metastability exchange. This approach requires the use of extremely low pressures of $^3He$, i.e., about 0.001 atm to about 0.01 atm, and does not involve the use of an alkali metal; the $^3He$ is polarized directly by the laser. Significant accumulation of hyperpolarized $^3He$ by this method is limited by the necessity of using huge pumping cells (i.e., about 1 meter long) and then compressing the gas to a useful level. The Becker et al. publication discloses an ingenious but technically difficult approach which employs large volume compressors made of titanium for compressing the gas to about atmospheric pressure. Unfortunately, manufacture and operation of such a system requires great engineering skill, limiting the reproducibility and operability of the system on a routine basis. The apparatus described by Becker et al. also requires significant amounts of floor space and cannot be moved. The Becker et al. paper also avoids the use of alkali metals in the pumping cells, and does not disclose any method of producing hyperpolarized noble gas by spin exchange. Hence, the Becker et al. paper does not resolve the complexity of manufacturing pumping cells in which an alkali metal is employed. As a result, this publication does not describe or suggest any method or apparatus related to the production and delivery of arbitrarily large or small quantities of hyperpolarized noble gas by spin exchange.

It was recently demonstrated that hyperpolarized noble gases can be imaged by nuclear magnetic resonance imaging (MRI) techniques. See U.S. Pat. No. 5,545,396. In addition, because the noble gases as a group are inert and non-toxic, it was found that hyperpolarized noble gases can be used for MRI of human and animal subjects. As a result, there exists a growing need for the generation of larger quantities of hyperpolarized noble gases. Moreover, because of medical and veterinary concerns, controlled uniformity and reliability in the purity of the gases and the amount of hyper polarization have become necessary. Also, the need for convenient and reliable generation of these hyperpolarized gases has become important for use in a clinical setting in which medical technicians, having little or no specific training in the laboratory techniques described above, are still able to provide discrete or continuous hyperpolarized noble gas samples to subjects undergoing MRI.

In view of the above considerations, it is clear that the apparatus and methods in use in the existing art are limited in a number of ways. For example, the existing art does not provide any practical means for refilling a spin exchange polarization chamber (cell) once it has been used. Most current chambers are either permanently sealed after the first filling or have been refilled with at best unsatisfactory results. Thus, it would be of benefit to develop means for effectively refilling a pumping chamber, or even for optically pumping in a continuous flow mode in the same chamber, so as to decrease costs of materials and personnel.

Moreover, even successful fills for the permanently sealed cells used previously were accomplished via a significantly different system. In the past, an expensive ultra-high vacuum system, with either oil-free pumps or cryotrapped oil-containing pumps, has been required in order to produce a sufficiently clean apparatus for filling high quality polarization chambers. Such a system is expensive (about $30,000), not very compact (3 ft by 6 ft footprint), and requires high maintenance by a trained vacuum technician. A new system, requiring only minimal maintenance and capable of being operated without specialized knowledge of vacuum technology, would be desirable. Also, a system having a more convenient size would be useful in clinical settings.

In addition, there has been no practical way to produce hyperpolarized gas in a continuous fashion. For each spin exchange hyper polarization procedure, a new sealed sample has had to be prepared and introduced into the hyper polarization apparatus. It would, therefore, be desirable to develop a system which overcomes this limitation to provide means for continuous hyperpolarization of flowing noble gas.

Systems for producing hyperpolarized gases have also been quite bulky, typically requiring separate rooms for their installation. Such systems are not transportable or installable as a single piece of apparatus in a room used for various other purposes. Thus, small, convenient hyperpolarizers would be advantageous. Also transportable systems would be of benefit in situations where space is a critical consideration.

Also, there has previously been no convenient way to store substantial quantities of hyperpolarized noble gases, especially $^{129}$Xe, for later distribution in discrete quantities of arbitrary amount (up to tens of liters of gas at atmospheric pressure). It would be important to overcome this limitation as well, to provide apparatus for continuous accumulation of a hyperpolarized noble gas, as well as storage and controlled release of the hyperpolarized gas on an as-needed basis, while still retaining substantial quantities of hyperpolarization.

SUMMARY OF THE INVENTION

Accordingly, as a result of the invention, there is now provided an improved apparatus and method for accumulating a hyperpolarized noble gas. In particular, there is provided apparatus for accumulating large quantities of high purity hyperpolarized noble gas for use in magnetic resonance imaging. Also a method and apparatus for continuous generation and accumulation of hyperpolarized noble gas, as well as for storage of large quantities of hyperpolarized noble gas.

The apparatus of the invention includes an accumulator system which permits the accumulation of hyperpolarized $^{129}$Xe in a continuous or semi-continuous mode. The accumulator system enables hyperpolarized xenon to be flowed through a cryotrapping reservoir and trapped efficiently and selectively as xenon ice before escaping. The accumulator also permits other gases to be passed through the system, thereby serving to selectively concentrate the hyperpolarized xenon. The accumulator preferably employs a cold trap reservoir, in which the trap is cooled to a temperature at or below the freezing temperature of xenon. The xenon passing into the accumulator then deposits efficiently on the walls of the accumulator reservoir in frozen form. Moreover, the accumulator permits xenon flowing within the reservoir to deposit on top of previously deposited xenon, thereby permitting the continuous or semi-continuous accumulation of the frozen gas. Because the solid form of hyperpolarized $^{129}$Xe has a much longer polarization lifetime than the gaseous form, the accumulator can serve as a storage device, allowing the accumulation of significant quantities of hyperpolarized gas for use at a later time. The invention further provides a method of using the variously described apparatus.

Optionally, the accumulator reservoir may be removable from the cooling apparatus and disconnectable from inflow and outflow conduits. Thus, a removable accumulation reservoir cartridge may be removed and stored separately in another cooling or refrigerating apparatus. In this way, the operation of the accumulator can be continued by installing another of the removable reservoir cartridges.

For purposes of accumulation of hyperpolarized $^{129}$Xe according to the invention, the hyperpolarization of xenon is preferably performed using xenon supplied in a gas mixture. The gas mixture includes xenon including at least a natural isotopic abundance of $^{129}$Xe. In addition, for purposes of enhancing the efficiency of spin-exchange polarization, a quenching gas, such as nitrogen or hydrogen, is also included in the gas mixture to suppress fluorescence of the alkali metal during the optical pumping procedure. It has now been observed that the hyperpolarization of high partial pressures of xenon is not as efficient as desired, i.e., high pressure xenon can inhibit its own hyperpolarization by depolarizing the alkali metal too efficiently. Low pressure hyperpolarization therefore, has been the requisite norm. A new method of improving the efficiency of xenon hyperpolarization according to the invention, however, includes using a buffer gas to broaden the band of wavelengths that can be absorbed by the alkali-metal vapor, thereby enhancing the efficiency of the hyperpolarization process. One preferred buffer gas is helium. The invention includes the use of a buffer gas different from the quenching gas, to solve the problem that certain quenching gases cause depolarization of the alkali-metal vapor at high pressures of the quenching gas. Accordingly, a preferred gas mixture according to the invention includes a minor amount of $^{129}$Xe, a minor amount of a quenching gas, and the balance helium.

Thus, the apparatus of the invention is beneficially employed in conjunction with a high capacity hyperpolarizer, in which a noble gas may be hyperpolarized in substantially larger quantities than has been possible in the past. This hyperpolarizer includes means for hyperpolarizing a noble gas in a continuous or at least semi-continuous manner. For example, the noble gas may be flowed through the hyperpolarizer's polarization chamber in a continuous mode, such that the rate of flow permits a substantial fraction of the nuclei to be hyperpolarized during their passage through the polarization chamber. Alternatively, in a semi-continuous (episodic or periodic) approach, the noble gas may be flowed into the polarization chamber in discrete volumes, hyperpolarized, and thereafter released to permit subsequent volumes of the gas to be treated. In this apparatus, individual cells do not have to be prepared, since the same chamber can be used by continuous flow-through or by repeated fillings and evacuations. Hence, the generation of relatively large quantities of the hyperpolarized noble gas is not impeded or otherwise limited by the need to prepare new hyperpolarization cells.

The invention also relates to a method of hyperpolarizing $^{129}$Xe, and accumulating substantial quantities of the hyperpolarized gas. Specifically, the method includes hyperpolarizing a target gas mixture, including a noble gas in minor proportion, flowing the hyperpolarized target gas mixture into an accumulator, and accumulating the hyperpolarized noble gas to the substantial exclusion of other gases in the gas mixture. Preferably, the method involves hyperpolarizing a minor proportion of $^{129}$Xe in admixture with a buffer gas such as helium, and a quenching gas such as nitrogen. While only minor amounts of the $^{129}$Xe are produced at any given moment, the target gas is flowed into an accumulator which causes the xenon to freeze while avoiding phase change in the other gases in the mixture. Thus, the xenon deposits in the accumulator reservoir in substantially purified form, while the other gases are selectively removed. Furthermore, the xenon can accumulate to yield far larger quantities of hyperpolarized gas than would otherwise be possible.

Turning now to particular embodiments of the invention, in one embodiment, the invention includes a method of accumulating hyperpolarized $^{129}$Xe. The method includes flowing a source gas, including hyperpolarized $^{129}$Xe, through accumulation means, and accumulating the hyperpolarized $^{129}$Xe in the accumulation means. Preferably, the accumulation method includes accumulating the $^{129}$Xe in accumulation means including:

a) an accumulation reservoir permissive to gas flow therethrough, and b) refrigeration means for refrigerating the accumulation reservoir to a temperature sufficient to cause $^{129}$Xe to accumulate in the accumulation reservoir in frozen form.

It is preferred that the method include accumulating the hyperpolarized $^{129}$Xe in an applied magnetic field. The preferred strength of the applied magnetic field is sufficient to maximize the spin-lattice relaxation time of the hyperpolarized $^{129}$Xe at the accumulation temperature. For example, the field should be at least about 500 G at liquid nitrogen temperatures. Lower temperatures typically require appropriately higher fields.

The method of the invention enables performing the accumulating for any given period, however, it is believed that because of relaxation of the hyperpolarized $^{129}$Xe, the hyperpolarized fraction of the net accumulated xenon ice will decrease when the accumulation period exceeds the maximum possible spin-lattice relaxation time of $^{129}$Xe at the temperature of the ice. Therefore, it is preferred that the xenon be collected for a period of up to about the maximum possible spin-lattice relaxation time of $^{129}$Xe at the temperature at which the $^{129}$Xe is accumulated. The use of lower refrigeration temperatures is associated with increased relaxation times, thereby permitting longer accumulation periods.

The source gas includes xenon having at least a natural abundance of $^{129}$Xe. More preferably, the xenon in the source gas is enriched for $^{129}$Xe above natural abundance levels. Due to specific limitations which have been identified in hyperbaric spin-exchange hyperpolarization of xenon, the xenon is preferably provided in a source gas which also comprises one or more other gases. Specifically, the method can be performed using a source gas which further includes an alkali-metal-fluorescence quenching gas, such as nitrogen or hydrogen. Also, the method can be performed using a source gas which includes a buffer gas capable of pressure broadening the optical absorption spectrum of the alkali metal atoms used in the spin exchange procedure. One preferred buffer gas is helium. Hydrogen can serve both as a quenching gas and a buffer gas to broaden the optical absorption line. Nitrogen is not as good a gas to broaden the optical absorption line as hydrogen or helium, because it causes substantial depolarization of the alkali metal atoms.

Preferably, the source gas which is flowed through the accumulator according to the invention includes nitrogen and helium in addition to the hyperpolarized $^{129}$Xe. This is principally due to the preference for a Xe:He:N$_2$ gas mixture for the production of the hyperpolarized $^{29}$Xe. More preferably, the source gas includes from about 0.1% to about 5% of hyperpolarized $^{129}$Xe, from about 0.1% to about 3% of N$_2$, and the balance being helium. Alternatively, the source gas can include from about 0.1% to about 5% $^{129}$Xe, from about 1% to about 30% H$_2$, with the balance being helium. A presently preferred source gas mixture includes about 1% of hyperpolarized $^{129}$Xe, about 1% of N$_2$, and about 98% of helium.

The method preferably permits accumulating the hyperpolarized $^{129}$Xe while at least substantially excluding accumulation of other gases. In this way the hyperpolarized $^{129}$Xe is substantially purified, overcoming low initial concentrations of xenon in a source gas which includes significant proportions of other gases.

The method of the invention preferably includes accumulating hyperpolarized $^{129}$Xe by means of a refrigeration system. One type of refrigeration system includes means for refrigerating the accumulation reservoir by means of a liquefied gas, such as liquid nitrogen or liquid helium. The reservoir in this type of system may be immersed in the liquefied gas, or may be maintained in contact with the cold vapor produced by the liquid. In still another approach, the method can employ refrigeration means which includes a closed-cycle refrigeration system. It is believed that lower temperatures are desirable for prolonging the lifetime of the hyperpolarized $^{129}$Xe.

This method of the invention preferably further includes hyperpolarizing $^{129}$Xe prior to accumulating the hyperpolarized $^{129}$Xe from the source gas. The hyperpolarizing preferably involves hyperpolarizing the $^{129}$Xe by spin exchange with an alkali metal, such as rubidium or cesium. Also, the hyperpolarizing procedure is preferably performed using a continuous flow of the source gas including the hyperpolarized $^{129}$Xe to permit accumulating of the hyperpolarized $^{129}$Xe for a period of up to about the maximum possible spin-lattice relaxation time for the $^{129}$Xe at the temperature of the accumulation means.

It is further desirable to supplement the method of the invention by storing the accumulated hyperpolarized $^{129}$Xe at a temperature of about or below the freezing point of $^{129}$Xe. Indeed, it is an advantage of the method that the storing of the accumulated hyperpolarized $^{129}$Xe can be accomplished at a location which is removed from (remote) from the location of accumulation. Thus, the accumulation reservoir, or the reservoir together with the refrigeration means, can be transported to another site for storage. This permits accumulation to be resumed to provide another quantity of hyperpolarized $^{129}$Xe. The storing of the accumulated xenon is preferably performed using a temperature lower than that employed for the accumulation. Also, it is preferred that the storage be performed with an applied magnetic field sufficient to maximize the spin-lattice relaxation time of the hyperpolarized $^{129}$Xe at the storage temperature.

In another embodiment, the invention also provides accumulator apparatus for continuous accumulation of hyperpolarized $^{129}$Xe. In this embodiment, the apparatus includes:

a) an accumulation reservoir for accumulating hyperpolarized $^{129}$Xe flowing therethrough, and b) refrigeration means for refrigerating the accumulation reservoir to a temperature sufficient to cause accumulation of hyperpolarized $^{129}$Xe in a frozen form.

Preferably, the accumulator apparatus further includes means for applying a magnetic field to the accumulation reservoir, more preferably a field sufficient to maximize the spin-lattice relaxation time of the hyperpolarized $^{129}$Xe at the accumulation temperature.

The apparatus also preferably includes refrigeration means for refrigerating the accumulation reservoir with liquid nitrogen, liquid helium or other liquefied gas.

Alternatively, the refrigeration means includes a closed-cycle refrigeration system.

More preferably, the apparatus further includes means for providing the hyperpolarized $^{129}$Xe. It is preferred that the apparatus includes means for hyperpolarizing $^{129}$Xe, preferably by means of spin exchange with an alkali metal. Preferred hyperpolarizing apparatus includes apparatus capable of delivering hyperpolarized $^{129}$Xe in continuous or pulsed flow modes.

The apparatus is preferably of modular design so that the accumulation reservoir is removable to permit storage of the frozen xenon at a remote location. Thus, the accumulation reservoir is desirably removable from the from the refrigeration means. Alternatively, when hyperpolarizing means are included, the accumulation reservoir can be removable from the hyperpolarizing means and the refrigeration means. In another alternative configuration, the accumulation reservoir and the refrigeration means are removable from the hyperpolarizing means.

In the apparatus of the invention, the accumulation reservoir is preferably sealable to prevent gas leakage either into or out of the reservoir. This is particularly important in the context of storing the reservoir following accumulation of the xenon. Accordingly, the accumulation reservoir is sealable by various means such as one or more valved gas ports to permit control of gas flow into and out of the reservoir.

The apparatus can further include means for subliming frozen xenon to provide gaseous xenon including hyperpolarized $^{129}$Xe.

In another embodiment, the invention provides apparatus for continuous production of hyperpolarized $^{129}$Xe. Here the apparatus includes:

a) source gas delivery means adapted for providing flowing $^{129}$Xe, b) hyperpolarization means for hyperpolarizing the flowing $^{129}$Xe to provide flowing hyperpolarized $^{129}$Xe, and c) accumulation means for accumulating the hyperpolarized $^{129}$Xe.

Preferably, the accumulation means includes:

a) an accumulation reservoir for accumulating the hyperpolarized $^{129}$Xe, and b) refrigeration means for refrigerating the accumulation reservoir to a temperature sufficient to cause $^{129}$Xe to accumulate in the accumulation reservoir in frozen form.

Also desirable is apparatus in which the accumulation means further includes means for applying a magnetic field, preferably sufficient to maximize the spin-lattice relaxation time of the hyperpolarized $^{129}$Xe at the accumulation temperature, to the accumulation reservoir.

The apparatus preferably includes hyperpolarization means which includes:

a) a polarization chamber for polarizing the flowing $^{129}$Xe; and b) a light source capable of delivering hyperpolarizing radiation into the polarization chamber.

The polarization chamber can be provided with amount of an alkali metal, preferably rubidium or cesium, sufficient to provide an alkali-metal vapor during a spin exchange hyperpolarization procedure. Alkali metal vaporizer apparatus and alkali metal refluxing apparatus may be incorporated to limit loss of the alkali metal in the flowing configuration.

The light source is preferably a laser, such as a laser-diode array, and is capable of delivering hyperpolarizing radiation sufficient to induce hyperpolarizing of the $^{129}$Xe by spin exchange with alkali metal atoms.

In a further embodiment, the invention provides a method for continuous accumulation of a hyperpolarized $^{129}$Xe. In this embodiment, the invention includes:

flowing a target gas including hyperpolarized $^{129}$Xe through accumulator means to accumulate the hyperpolarized $^{129}$Xe, wherein the accumulator means includes:

a) an accumulation reservoir for accumulating $^{129}$Xe; and b) refrigeration means for refrigerating the accumulation reservoir to a temperature sufficient to cause $^{129}$Xe to accumulate in the accumulation reservoir, and c) means for applying a magnetic field to the accumulation reservoir.

In another embodiment, the invention provides a method for continuous accumulation of hyperpolarized $^{129}$Xe, including:

a) flowing a target gas including $^{129}$Xe through hyperpolarization means, b) hyperpolarizing the $^{129}$Xe by means of spin exchange with an alkali metal in the hyperpolarization means to provide hyperpolarized $^{129}$Xe in the target gas, and c) flowing the target gas through accumulator means to accumulate hyperpolarized $^{129}$Xe in frozen form;

wherein the accumulator means includes:

1) an accumulation reservoir for accumulating the frozen hyperpolarized $^{129}$Xe; and 2) refrigeration means for refrigerating the accumulation reservoir to a temperature sufficient to cause $^{129}$Xe to accumulate in the accumulation reservoir in frozen form.

Moreover, the invention also provides an embodiment including accumulator apparatus for the accumulation of hyperpolarized $^{129}$Xe, including:

a replaceable accumulation reservoir adapted to permit flow therethrough of a gas including hyperpolarized $^{129}$Xe, wherein the replaceable accumulation reservoir is adapted to replaceably engage and operate with refrigeration means for refrigerating the accumulation reservoir to a temperature sufficient to accumulate frozen hyperpolarized $^{129}$Xe.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

Figure 1:
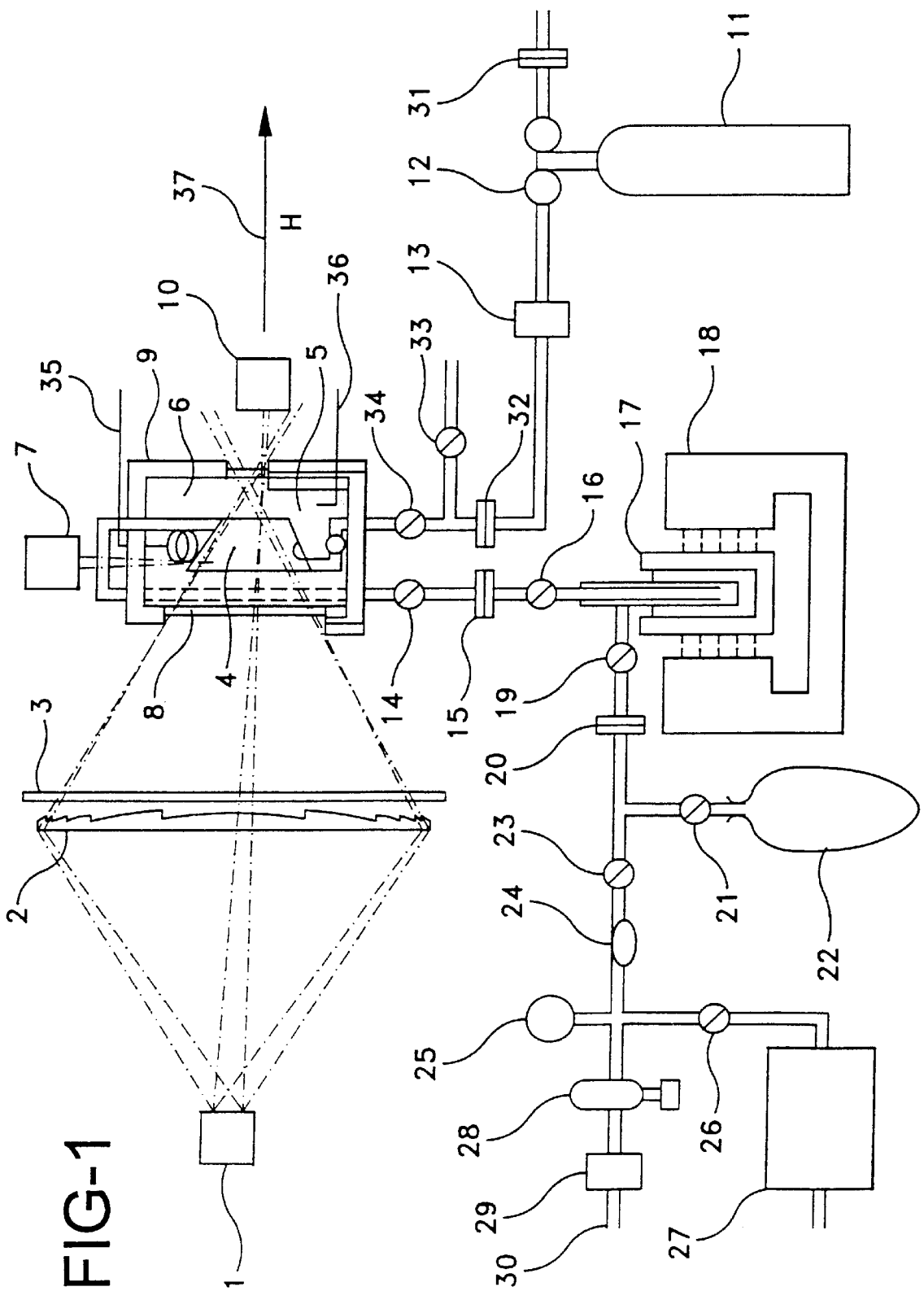
FIG. 1 is a schematic diagram of a cryotrapping accumulator according to the invention, in conjunction with a hyperpolarizer to provide hyperpolarized $^{129}$Xe.

FIG. 1 illustrates an integrated hyperpolarizer and accumulator system useful for generating and accumulating large quantities of hyperpolarized $^{129}$Xe according to the invention. In this Figure, a hyperpolarizer unit is shown which includes several major subsystems, including an MRI gas delivery subsystem through which the polarized gas can be delivered as needed for imaging studies.

In FIG. 1, a laser diode array 1, has an output power of from about 100 W to about 500 W and emits radiation of wavelength λ suitable for absorption by an alkali metal. The wavelength spread Δλ is about 2 nm FWHM, with a linear polarization of about 95% or greater. Because of the large spread in wavelength, this type of laser is referred to herein as a "broad-band" laser. In an alternative embodiment, two lasers pumping from opposite sides of the pumping cell 4 can be used, with appropriate redesign of the cell 4 and the optical diagnostics system 10.

An aspheric Fresnel lens 2 (typically plastic) directs most of the light from the diode laser array 1 into the optical pumping cell 4. An image of the diode face is formed just beyond the end of the optical pumping cell 4. Although the Fresnel lens is inexpensive and well adapted to currently available diode laser arrays, different optics may be more appropriate for future lasers which may have higher intrinsic brightness than those available today.

Quarter wave plate 3 converts linearly polarized light from the diode laser array to circularly polarized light. As shown, a plastic quarter wave plate is positioned just past the Fresnel lens 2 where the laser beam has expanded so much that heating of the lens and the wave plate is not a problem. The light from the laser 1, which is already linearly polarized to a high degree, can be passed through a linear polarizer (not shown) before it reaches the quarter wave plate 3 if the natural linear polarization is not sufficient.

Optical pumping cell 4 is shown, provided with saturated alkali-metal vapor, e.g., Rb or Cs, and an optimum gas mixture of $^{129}$Xe, $N_2$ and He, as described below in connection with the premixed gas tank 11. The cell 4 has the shape of a truncated cone to accommodate the converging light from the lens 2. Refluxed alkali metal from the exit pipe 6 drops back through the cell and collects in the vaporizer 5. The cell and associated piping must withstand the high pressure of premixed gas, typically from above about 1 atmosphere to about 30 atmospheres. High gas pressure inside the cell is important to permit efficient absorption of the broad-band light from a diode laser.

A vaporizer 5 is provided upstream from the pumping cell 4, for loading the flowing gas mixture with alkali-metal vapor prior to the gas's entry into the cell. The vaporizer 5 can be made of crumpled wires of copper or other non-magnetic metal or sintered metal that is readily wetted by liquid alkali metals (e.g., a metallic sponge). The vaporizer 5 is soaked with liquid alkali metal, and stuffed into a receptacle of appropriate materials and dimensions to ensure full loading of the gas with vapor. The flow velocity of the gas, the distance through which it flows, and the pore diameter of the "sponge" are adjusted to ensure that the gas is fully saturated with alkali-metal vapor before it enters the optical pumping cell.

The vaporizer 5 is replenished by gravity flow of condensed alkali metal from a refluxing outlet pipe 6, which leaves the cell in a substantially vertical orientation. The refluxing outlet pipe 6 is included to condense alkali metal from the exiting gas. The dimensions and flow velocity are adjusted to ensure that most of the alkali metal condenses and drips back into the optical pumping cell by gravity flow, eventually returning to the vaporizer.

A fluorescence monitoring detector 7, e.g., including a charge-coupled-device (CCD) camera and appropriate filters, is provided to observe the weak, unquenched $D_2$ fluorescence from the optically pumped alkali-metal vapor. The fluorescence monitoring arrangement can be adjusted for use with two lasers pumping from either side of the cell.

Insulating window 8 is provided to permit pumping light to enter the oven and the optical pumping cell. This window and other light-transmitting surfaces may be provided with an anti reflection coating. Similar windows are provided for the fluorescence monitor 7 and the optical multichannel analyzer (OMA) 10.

Oven 9 is provided to keep the optical pumping cell at a temperature appropriate for absorbing most of the useful light from the diode laser. Typical operating temperatures for rubidium are from about 100° C. to about 200° C. Somewhat lower temperatures are appropriate for cesium which is more easily volatilized. The oven can be heated by flowing hot air or by internal, non-magnetic electrical heaters.

Optical multichannel analyzer (OMA) 10 for measuring the efficiency of absorption of light from the broad-band diode laser array. A different arrangement of the OMA is required if the cell is pumped from both sides.

A high-pressure tank 11 is included to maintain a premixed target gas at a pressure of several hundred atmospheres. Preferred target gas constituents, by partial pressure, are:

a. from about 0.1% to about 5% $^{129}$Xe (or xenon of at least about natural isotopic composition) for hyperpolarization in the optical pumping cell 4 and accumulation in the xenon accumulator 17;

b. from about 1% to about 3% $N_2$ for quenching fluorescence in the optical pumping cell 4. $H_2$ may be used at somewhat higher partial pressures (e.g., from about 1% to about 30%) in place of $N_2$ to take advantage of the smaller spin depolarization cross-sections of alkali-metal atoms in $H_2$ gas compared to $N_2$ gas;

c. the balance of the gas is a buffer gas, preferably He, for pressure broadening the optical absorption lines of the alkali-metal atoms in the optical pumping cell 4. The He gas pressure is adjusted to ensure that it causes negligible spin depolarization compared to the xenon. Other gas mixtures may be employed impart quenching and pressure-broadening qualities to the target gas.

A pressure regulator 12 is employed to reduce the very high pressure of the premixed gas in the storage tank 11 to a pressure appropriate for the optical pumping cell 4. This is typically from about 10 to about 30 atmospheres, depending on how much pressure broadening is needed for optimum use of the broad-band laser light.

Gas purifier (getter) 13 is used to remove trace impurities, mainly water vapor, from the premixed target gas stream.

As shown, the accumulation reservoir 17 includes a counterflow cold trap—cooled by liquid nitrogen or some other cryogen in a Dewar vessel. Closed-cycle refrigerators can also be used for cooling.

Detachment point 15, together with the detachment point 20, permits the removal of the accumulation reservoir 17. Valve 14 isolates the optical pumping cell 4 from the detachment point 15, and controls flow therebetween. Valve 16 is used to isolate the accumulation reservoir 17 from detachment point 15.

A permanent magnet 18 is provided to produce a static field of greater than about 500 Gauss (0.05 T) at the location of the frozen xenon in the accumulator reservoir. A field this large is adequate to obtain the longest possible spin-lattice relaxation times (e.g., about 3 hours at liquid nitrogen temperatures). For lower condensation temperatures, where much longer spin-lattice relaxation times are attainable, larger magnetic fields are needed. The magnet may also be contained inside the cryogenic assembly and kept cool along with xenon accumulation reservoir.

Valve 19 is employed to isolate the xenon condenser 17 from the detachment point 20, which together with detachment point 15 permits removal of the xenon condenser 17.

Valve 21 is used to release sublimed hyperpolarized $^{129}$Xe gas to transfer bag 22 or to any other container for transport of hyperpolarized $^{129}$Xe gas at atmospheric pressure for various uses, e.g., MRI of patients, non-destructive evaluation, etc. Hard-walled containers can be used to transport the hyperpolarized $^{129}$Xe gas at other pressures.

Valve 23 isolates the xenon accumulator 17 during sublimation of the condensed xenon and gas transfer to the bag or other receptacle 22.

Glass-to-metal seal 24 is provided, with the piping on the pump side of the seal preferably being stainless steel or other metal. On the xenon-condenser side of the seal, the piping is glass. Similar glass-to-metal seals on the input side of the gas flow and appropriate stress-relieving bellows are not shown, but are normally to be preferred.

Pressure gauge 25 is used to monitor and control pressure during the accumulation phase.

Pump 27, isolated by valve 26, is used for evacuating any remaining He and $N_2$ from the xenon condenser 17 at the end of the accumulation period.

A needle valve 28 or other flow control device is included to permit waste He and $N_2$ gas to vent to the room or to a recovery container for reuse. This valve 28 controls the flow rate through the optical pumping cell 4. The venting rate is adjusted to optimize the preparation of hyperpolarized $^{129}$Xe according to principles we have developed. Flow of the gas is monitored by flow meter 29.

A vent 30 is provided, leading to the atmosphere or to a collection receptacle for spent He and quenching gas (e.g., $N_2$ or $H_2$).

Port 31 is included for purging the gas lines with clean gas (e.g. argon, helium or nitrogen) through the vent 24 after the tank of premixed gas is attached. Vent 33 permits release of the purging gas introduced at the port 31.

Attachment point 32 is supplied for connecting the pre-mixed gas supply to the optical pumping cell. Valve 34 isolates the optical pumping cell during purging of the gas-supply piping.

A nuclear magnetic resonance pickup coil 35 is also included to monitor $^{129}$Xe polarization in the pumping chamber, which is useful for optimizing the gas flow rate.

Temperature sensor 36, e.g., a resistive temperature device (RTD), is employed to monitor the temperature of the oven.

A static magnetic field 37 is also illustrated. The source is not shown, but we have successfully used either Helmholtz coils or the fringing fields of a magnetic resonance imaging magnet or a combination of the two.

A control subsystem (not shown) is generally desirable as a unified computer-software and hardwired subsystem which is used to control and monitor the different processes occurring in the various subsystems.

While described with particularity hereinbelow, the manufacture and operation of high capacity hyperpolarization systems, such as are suitable for use in conjunction with the accumulator apparatus of the invention, are described in more detail in co-pending U.S. patent application Ser. No. 08/622,863, filed on even date herewith, entitled "High-Volume Hyperpolarizer for Spin-Polarized Noble Gas." The entire disclosure of that application is incorporated herein by reference.

One implementation of a polarization chamber is shown in FIG. 1. As the chamber in which the optical pumping and spin exchange takes place it must satisfy a number of requirements. For example, the pumping chamber must hold an appropriate amount of polarizable gas in a substantially leak-tight environment. The gas pressure in the chamber is maintained according to the requirements of the apparatus, preferably being maintained at a pressure above atmospheric pressure (also designated herein "hyperbaric") up to about 30 atmospheres (atm), and more preferably from about 8 atm to about 12 atm for a glass cell. The gas pressure may be outside (above or below) this range, as required. A presently preferred pressure is about 10 atm, which reflects the structural limitations of glass, the material most typically used in the manufacture of polarization chambers. Higher pressure or gas density could be used in other polarization chamber structures.

The pumping chamber should admit hyperpolarizing radiation from the laser source(s). Preferred structures of the chamber include conical or truncated conical (frustoconical) structures, although in certain configurations a cylindrical cell is suitable. Preferably, the chamber is designed in conjunction with the laser system to maximize light delivery into the chamber and throughout its interior, to maximize the efficiency of the hyperpolarizing procedure.

A preferred type of pumping chamber (not shown in FIG. 1), has two light ports (windows), for admitting hyperpolarizing radiation into the cell from two lasers arranged to emit along the same axis. Regardless of whether one or more than one light port is employed, the ports are preferably at least substantially transparent to light at and/or near the wavelength of the optical pumping transition line of the alkali metal being used for optical pumping (i.e., "hyperpolarizing radiation"). For example, the wavelength of the $D_1$ transition in rubidium is 794.7 nm, and the light ports suitable for use with rubidium should be at least substantially transparent to light at this wavelength. Optimization of pumping efficiency would require that the light ports be as transparent as possible to light of the requisite wavelength, i.e., absorption of the hyperpolarizing radiation should be minimized. They may be antireflection-coated to maximize light transmission. When two ports are employed in conjunction with opposed lasers, the interior surfaces of the ports may be made reflective to retain the light in the interior of the chamber.

The volume-averaged relaxation time of the nuclear polarization of a gas in the pumping chamber must be sufficiently slow compared to the spin-exchange rate between the alkali metal atom and the noble gas nucleus to allow the desired level of polarization in the cell to be attained. The materials and design of the polarization chamber must, therefore, be selected with care. For example, the pumping chamber should be chemically compatible with alkali-metals, preferably being compatible with alkali metals at the elevated temperatures appropriate for optical pumping (e.g., up to about 200° C. or more). In addition, if an NMR polarimetry system is used to monitor the hyperpolarization procedure, it is preferred that the pumping chamber walls not interfere substantially with the rf field required for polarimetry.

The particular implementation of the pumping chamber will depend on the type of gas being polarized. As noted above, polarization chambers suitable for use in accordance with the invention are typically made of glass. The glass should be resistant to the alkali metal(s) employed in the spin exchange process. Such glasses are exemplified by aluminosilicate glasses (such as Corning 1720), or metal-sealing borosilicate glasses (such as Corning 7052 or Schott 8502). For lower temperature applications, standard borosilicate laboratory glassware, e.g., Pyrex®, Duran®, can be used. Other pumping chamber designs, capable of higher pressure operation, include metal structures fitted with glass light ports. Moreover, in another approach, a cell can be surrounded with hot high pressure gas or a transparent liquid (e.g., pump oil) to minimize the pressure differential across the glass cell walls and windows.

As shown in FIG. 1, the pumping chamber also desirably has separate resealable (e.g., valved) inlet and outlet ports, which allow continuous or episodic flowing removal and replacement of the gas being polarized. Any suitable gas ports permitting flow control can be employed. Alternatively, the chamber can have a single gas port through which gas is flowed into and out of the cell periodically. In FIG. 1, the gas handling system includes valves 14 and 34 to isolate the optical pumping cell from the accumulator and the gas supply as needed.

The resealable gas ports include valve means, such as o-ring valves, for controlling the flow of gas. Typically, these valves have Pyrex® glass bodies and stems, thereby permitting manufacture of the polarization chamber with the inlet and outlet ports integrated therewith. Such valves are fitted with flexible and elastic seals which are also resistant to alkali metals. Such seals are typically o-rings, and can be made of various polymeric materials such as ethylene-propylene copolymers. Resistance of the o-rings to alkali attack is an important characteristic since oxidation of the pumping chamber can occur should oxygen enter the chamber through failed o-rings.

The valves in the resealable gas inlet and outlet apparatus are separated from the main body of the pumping chamber by conduits, preferably tubes made from glass similar to that used for the polarization chamber. These tubes allow the heat sensitive o-ring materials to be thermally separated from the main body of the cell and the oven surrounding the cell, which, during the polarization process, is often heated to above the o-ring's limit. The tubes also reduce the net polarization relaxation due to the valve body, since at the high operating gas pressures, diffusion down the length of the tubes is slow compared to the depolarization time constant of the bulk volume (which is dependent upon the ratio of tube volume to total volume). With this arrangement, valves constructed of non-ferrous metals could also be used.

We have found that gas depolarization by the pumping cell can be advantageously reduced. For example, metal-film coatings (gold, alkali-metals, etc.) on the cell walls may improve polarization lifetimes and reduce the effort required in cleaning and fabricating cells. Polymeric coatings such as those described in U.S. Pat. No. 5,612,103, can also be employed beneficially. Other methods are available as well, and are detailed in the aforementioned U.S. patent application Ser. No. 08/622,863

The receiving reservoirs for the accumulator apparatus of the invention may be manufactured to the same exacting standards required for the pumping chambers, except that the requirements of alkali-metal chemical resistance and transparency to the optical-pumping laser light can be relaxed. We have found that because the relaxation of the hyperpolarized $^{129}$Xe is so efficiently depressed in the frozen state, the quality of manufacture of the walls of the accumulation reservoir is of lesser importance. This feature, therefore, enables lower quality standards to be observed, with concomitant cost savings.

We find that alkali-metal vapor tends to be lost from a flowing gas polarization chamber during even modest gas flows (10–20 cm$^3$/min) if significant precautions are not taken. This has previously been a substantial impediment to the development of refillable or continuous flow cells. We have observed, for example, that the rubidium absorption resonance and $D_2$ resonance can completely disappear under unfavorable conditions. Our study indicates that the major source of rubidium loss in a flowing gas system is due to gettering of impurities (presumably $H_2O$ and $O_2$) by the rubidium vapor. Small amounts of these impurities in the supply gas would ordinarily have only a vanishingly small effect on the rubidium in a sealed cell. Flow of gas, however, appears to provide a continual fresh supply of such alkali-metal-reactive impurities into the polarization chamber, resulting in continuing and substantial diminution of available alkali vapor. Our present understanding is based on our finding that this loss of rubidium vapor can be substantially prevented by installing an in-line gas purifier, such as one of the nitrogen purifiers (getters) available from Ultra-Pure Systems, Inc. Such purifiers have been found to clean the feed gas sufficiently so that rubidium vapor loss is virtually eliminated at a wide range of flow rates. Such purifiers are typically designed for the purification of nitrogen, but they also pass the noble gases without problem, and have been found to be ideally suited for purification of, for example, a He:Xe:$N_2$ mixture preferably employed according to the method of the invention.

Another, albeit less significant, loss of rubidium occurs due to rubidium leaving the cell as gas is flowed through the cell. We have overcome this problem in two ways. First, by ensuring that the temperature of the conduit leading away from the pumping cell is low enough, the rubidium will deposit on the conduit walls. Room temperature is normally adequate. No additional filter or trap is required, although a cold trap may be employed to ensure complete rubidium removal in medical applications. More preferably, however, the alkali metal may be maintained in vapor phase by a refluxing system.

As mentioned briefly above, FIG. 1 also shows the oven 9 which houses the polarization chamber 4. The optical pumping oven operates in a temperature range which is limited by loss of alkali-metal vapor polarization at unduly high temperatures. Maximizing the temperature without sacrificing alkali metal polarization serves to maximize the spin exchange rate, allowing for faster accumulation of polarized noble gas. Typically, the temperature range for the oven is from about 80° C. to about 200° C. A preferred temperature is in the range of from about 105° C. to about 150° C. For example, a temperature of about 150° C. provides a Rb—$^{129}$Xe spin exchange time of about 22 s, and an average rubidium polarization of about 50%. About 20–30% of the laser light is absorbed by the rubidium at this temperature. A temperature of about 130° C. may be preferred since the $^{129}$Xe NMR signal drops precipitously at higher temperatures. At 130° C., the Rb—$^{129}$Xe spin exchange time is about 65 s, roughly a factor of three lower than the time at 150° C. Accordingly, flow rates would have to be lower at lower temperatures, resulting in lower yields of polarized $^{129}$Xe. It has also been found that laser-induced heating causes a higher (~20° C. higher) effective cell temperature (and thus a higher rubidium number density [Rb]) than is reflected by the oven thermometer. Similar considerations apply when using cesium or other alkali metal in the pumping chamber.

By controlling gas flow rate and temperature in the polarization chamber, the degree of polarization and total volume of $^{129}$Xe produced can be adjusted. For a given available laser power and bandwidth, the temperature of the pumping chamber will be set as high as possible without significant sacrifice to the volume-averaged polarization of the alkali-metal vapor. This optimization determines the spin-exchange rate $\gamma_{SE}$ at which polarization is transferred to the $^{129}$Xe. The flow rate will preferably then be adjusted so that a $^{129}$Xe atom spends on average about 1–3 spin exchange time constants ($1/\gamma_{SE}$) in the polarization chamber. A hotter chamber will result in faster spin exchange, thus allowing higher flow rates of $^{129}$Xe. Flow settings can be verified by comparing the $^{129}$Xe NMR signal against the flow rate. If the flow is too fast, the $^{129}$Xe signal will drop because the sample does not have a chance to fully polarize.

The oven should be constructed so as to minimize the creation of magnetic-field gradients capable of inducing nuclear relaxation in the noble gas. Preferably, the oven is constructed of materials that do not create gradients sufficient to induce significant nuclear relaxation in the noble gas. The oven materials should also retain substantial structural integrity at temperatures up to at least about 250° C. High temperature plastics or aluminum are suitable choices. Ferromagnetic materials such as steel generate magnetic field gradients which can rapidly depolarize the noble gas, and are therefore less desirable materials.

As noted above in reference to FIG. 1, the illustrated oven 4 is provided with laser windows positioned which permit laser light to pass into and out of the oven along the optical axis of the system. (The optical axis is defined as the path, containing the laser, optics, and the cell, along which the laser light travels.) The oven is preferably oriented so that the optical axis is aligned with the direction of the applied magnetic field necessary for optical pumping. The oven's windows allow the polarization chamber to be illuminated by laser light from either side along the optical axis. Preferably, these windows do not significantly impair the transmission of the laser light through reflection and/or absorption. They may be anti reflection-coated to maximize light transmission.

Again referring to FIG. 1, the oven 9 may also be equipped with a fluorescence observation window. Preferably, the observation window is oriented to permit visualization of the polarizing chamber from a position substantially perpendicular to the optical axis. This window allows the observation of $D_2$ resonant fluorescence resulting from optical pumping of an alkali-metal vapor. The fluorescence visualization means typically includes a video camera and monitor, equipped with a $D_2$ filter, for observing the fluorescence. The image can be used to tune the laser wavelength, to optimize the optical pumping temperature, as well as to align the laser.

The oven should be heated by means of materials and in a manner that satisfy the same conditions for minimizing magnetic-field gradients as described above. While not shown in FIG. 1, in a preferred embodiment, compressed air is passed over a filament heater situated at a distance from the oven (to minimize field gradients). The hot air is then flowed through the oven to attain the desired temperature. A temperature controller actuates the heater based on the reading of a temperature sensor inside the oven. Alternatively, a high rf electrical heater may be employed.

The gas handling and purification system can take various forms. Ideally, the system introduces the correct mixture of gases into the polarization chamber while simultaneously insuring sufficient purity in the gas stream to prevent significant degradation of the quality of the polarization chamber. The polarization-chamber quality is determined by the $T_1$ (polarization lifetime) of the hyperpolarized gas within it. It is known that the polarization chamber quality is affected both by gaseous impurities and by contaminants on the walls.

The polarization process requires both the polarizable noble gas (typically anywhere from 0.1 atm to tens of atm) and a small amount (generally 10 to 100 Torr) of a quenching gas (usually nitrogen, but perhaps hydrogen or others). The quenching gas improves the efficiency of the optical pumping process. For hyperpolarizing $^{129}$Xe, it is preferred to also include a large amount of a buffer gas (generally from about 1 atm to a few tens of atm), which acts to broaden the alkali-metal absorption line and to improve the polarization efficiency.

Accordingly, the gas handling system should enable delivery of mixtures of the gases in an easily controllable manner. For example, the system can include separate gas containers for each gas, with conduits, flow meters, regulators, pressure gauges, etc., as needed. Separate pathways for introducing the low-pressure ($N_2$) and high-pressure gases may be included to minimize the risk of pressure-induced rupture. As was mentioned above, it has been found that chemical or cryogenic getters should be placed in the gas flow lines as needed to increase the gas purity. Since varying purities of gas are available, the amount of additional purification will be established based on measurements of the polarization-chamber degradation vs either number of times refilled (if discrete charges are used) or total operating time (if a continuous-flow system is used). Even high purity gases however, have been found to contain enough impurities, such as $O_2$ and $H_2O$, to cause significant degradation of the cells within a relatively short period of flow or after a few refills.

In a highly preferred embodiment, a system for delivering a premixed target gas is employed. In this case, the gas mixture is supplied directly to the polarization chamber without need for adjusting relative flow rates. This simplifies the operation of the system, and renders the polarization process more reproducible and consistent. Suitable gas mixtures are discussed elsewhere herein, and may be obtained from commercial sources by special request.

The hyperpolarization procedure should be monitored by determining the condition of the gas contents as the hyperpolarization proceeds. NMR polarimetry is a preferred method for monitoring the gas polarization in the polarization chamber (cell). The polarimetry subsystem functions according to typical NMR principles. Alternatively, a separate outlet bulb can be fitted to the polarization chamber to permit accumulation of a test sample of the polarized gas. The bulb can be measured in an Adiabatic Fast Passage (AFP) apparatus, which can yield much better NMR signals than pulsed NMR on the pump chamber, even though typically requiring larger sample volumes. This apparatus can be calibrated to provide an experimental measurement of the $^{129}Xe$ polarization, which can be used to further refine the adjustment of the accumulation parameters.

The entire hyperpolarization system can be run from a desktop computer equipped with a few special circuit boards. One such board generates the necessary radio frequency pulses through Direct Digital Synthesis (DDS). Another desirable circuit board is an analog-to-digital converter (ADC. board), which digitizes the signal.

The laser subsystem of the hyperpolarization apparatus supplies the photons (hyperpolarizing radiation) necessary to the optical pumping process. Preferably, the photons are supplied by one or more laser-diode arrays producing continuous wave (cw) power. However, any laser system that provides sufficient power at the alkali-metal $D_1$ or $D_2$ lines may be acceptable. High pressure operation such as that described herein, however, has been found to require lasers capable of delivering more than 10 W, and preferably more than 50 W of power. Conventional lasers capable of delivering such power are prohibitively expensive to purchase and operate. Moreover, such lasers are bulky and require expensive and more or less permanent installation. For transportable or integrated hyperpolarization units, such lasers are too unwieldy. In such embodiments, the laser-diode arrays become highly preferred because of their compactness and efficiency, as well as their relative cheapness to acquire and operate.

Unlike conventional lasers which emit coherent light of a single wavelength (extremely narrow profile), diode array lasers are broad-band devices whose emissions have a spectral width. i.e., typically emitting light at a continuous band of wavelengths. Normally, this spectral width is relatively narrow, appearing as a broadening around some principal wavelength, and being only about 1–5 nm wide. Lower power GaAlAs diode arrays have been employed for spin exchange polarization of $^3He$. Chupp et al., *Phys. Rev. A* 40(8):4447–4454 (1989) describes the use of an approximately 1-W diode array, and Cummings et al., *Phys. Rev. A* 51(6)4842–4851 (1995) describes a 20-W diode array. For the method and apparatus of the present invention, the power of the diode arrays is preferably significantly larger, being above about 50 W, and more preferably above about 100 W.

The choice of laser emission wavelength $\lambda$ is determined by the choice of the alkali metal used for spin exchange. For rubidium, $\lambda$ should be about 795 nm, while for cesium, $\lambda$ should be about 894 nm. Thus, for rubidium, the laser can be a GaAlAs laser, while for cesium, it can be an aluminum-free laser, e.g., InGaAsP. A currently preferred laser diode array (available from Opto Power of Tucson, Ariz.) develops about 125 W of continuous wave (cw) power, can be tuned to a peak wavelength of 794.44 nm, and exhibits about 2 nm full spectral width at half maximum (FWHM).

Should lasers with narrower bandwidths become competitive (efficiency, cost, etc.) with conventional arrays in the future, less line-broadening buffer gas would be needed than for the presently available lasers mentioned above. This would permit use of higher proportions of xenon in the target gas mixture, which in turn would improve the yield of the accumulator apparatus. Lower pressure operation would also simplify some engineering problems with respect to the hyperpolarizer.

Previously, it has been recognized that hyperpolarized $^3He$ can be produced at high polarizations by means of spin exchange at high pressures (~10 atm). We have found however, that this is not possible when using high pressures of $^{129}Xe$. Specifically, the efficiency with which xenon depolarizes rubidium vapor is surprisingly high. We estimate that, neglecting molecular contributions, 0.1 atm of xenon has about the same spin destructive effect as 270 atm of helium. As a result, it is now believed that xenon pressures in excess of about 1 atm will result in very low rubidium polarizations for all but the most intense (i.e., thousands of watts) pump lasers.

For example, for a diode laser, a laser intensity of about 20 $W/cm^2$ (or 100 W/5 $cm^2$) would result in a Rb electronic polarization of only about 25% at the front of a chamber containing 10 atm of xenon. This polarization level only decreases toward the back of the chamber so that only small polarization volumes can be tolerated, with correspondingly small yields of polarized $^{129}Xe$.

The use of lower pressures of xenon can result in higher Rb polarizations, but at a substantial penalty. Low gas pressures give narrow Rb $D_1$ resonance lines and thus allow only a tiny fraction of the broad spectral output of the diode array (2 nm FWHM) to be used. Furthermore, the spectral hole burning that results from a narrow $D_1$ resonance again means that only very small volumes of Rb can be polarized, yielding small quantities of polarized $^{129}Xe$. For example, a 20 $cm^3$ cell containing 0.5 atm of xenon, and having a wall relaxation of time of 1000 s will at optimum give a $^{129}Xe$ polarization of 56%, while using only 2.3 W of 100 W incident on the cell. The resulting 10 $cm^3$ of polarized gas (at 1 atm) is not sufficient for most applications of interest.

In typical hyperpolarization procedures, unpolarized $^{129}Xe$ is placed in a sealed pumping cell along with a few tens of Torr of a quenching gas (often nitrogen) which quenches the fluorescence of laser-excited rubidium atoms, thereby aiding the optical pumping process. We have unexpectedly found, however, that a buffer gas can be added to the sample to broaden the alkali-metal resonance line, allowing for more efficient absorption of the broad spectral output of current high-power laser-diode arrays. Without this high-pressure buffer gas, very little (about 1%) of the light from the diode laser can be absorbed because of the broad spectral bandwidth of the diode laser array (2 nm or more) and the very narrow (0.01 nm) absorption bandwidth of alkali-metal atoms at low pressure. To achieve the desired effect, however, the buffer gas should not induce significant spin destruction of either the alkali-metal vapor or the $^{129}Xe$ during optical pumping. A preferred buffer gas is helium (primarily $^4He$), but other gases, for example, hydrogen, having similar properties may be employed. We have observed that increased pressures of the buffer gas induce the absorption band of rubidium to broaden, and gas pressures of order 10 atm or more are preferred to achieve the desired broadening. Due to xenon's inherent capacity to destroy alkali-metal polarization, however, it is believed that samples containing around 10 atm or more of pure xenon would not be usable. By contrast, it has been found that helium is quite non-destructive to the polarized alkali-metal spins and can be used as a line-broadening agent without penalty.

Accordingly, preferred gas mixtures for hyperpolarization according to the method of the invention would include a substantial proportion of the buffer gas, e.g., helium, with a minor but significant amount of $^{129}$Xe. For example, the mixture can include from about 0.1% to about 5% of xenon containing at least a natural isotopic abundance of $^{129}$Xe, from about 0.1% to about 3% of $N_2$, with the balance being helium. Most preferably, the mixture includes about 1% of $^{129}$Xe, about 1% of $N_2$, and about 98% helium. Alternatively, if the quenching gas is hydrogen, from about 1% to about 30% of the gas mixture should be hydrogen, with a corresponding reduction in the net proportion of helium.

The low partial pressures of xenon used in the preferred method give rise to several problems. First, polarized $^{129}$Xe must be separated from the $^4$He to attain useful concentrations of $^{129}$Xe. Second, the polarized $^{129}$Xe must be pressurized so that it can be extracted from the polarization apparatus. Third, while high $^{129}$Xe polarizations are attained on very short timescales, the yield of polarized gas from the pump chamber is very small. We have now found that freezing the polarized $^{129}$Xe into a solid (T$\leq$160 K) solves all three of these problems.

To produce laser-polarized $^{129}$Xe in significant quantities, we have taken advantage of the extremely long spin-lattice-relaxation times $T_1$. of solid $^{129}$Xe. It has been demonstrated that once polarized, $^{129}$Xe can be frozen into a solid with little loss of polarization. As detailed in Gatzke et al., *Phys. Rev. Lett.*, 70(5):690–693 (1993), the relaxation times of solid phase $^{129}$Xe are much longer than those achieved thus far in the gaseous phase.

It is now possible, by means of the accumulator apparatus of the invention, to take advantage of the properties of xenon ice. Specifically, it is now recognized that the three-hour relaxation time of $^{129}$Xe in ice at liquid nitrogen temperatures permits the pumping and continuous accumulation of polarized $^{129}$Xe for up to three hours at a time at these temperatures. The use of even lower temperatures can extend the potential accumulation period further.

A cryogenic accumulator for the accumulation of storable quantities of $^{129}$Xe according to the invention is schematically illustrated in FIG. 1 and its features are briefly described hereinbelow. By controlling gas flow rate and temperature in the polarization chamber, the degree of polarization and total volume of $^{129}$Xe produced can be adjusted. For a given available laser power and bandwidth, the temperature of the pumping chamber will be set as high as possible without significant sacrifice to the volume-averaged polarization of the alkali-metal vapor. This optimization determines the spin-exchange rate $\gamma_{SE}$ at which polarization is transferred to the $^{129}$Xe. The flow rate will preferably then be adjusted so that a $^{129}$Xe atom spends on average about 1–3 spin exchange time constants ($1/\gamma_{SE}$) in the polarization chamber. A hotter chamber will result in faster spin exchange, thus allowing higher flow rates of $^{129}$Xe. Flow settings can be verified by comparing the $^{129}$Xe NMR signal against the flow rate. If the flow is too fast, the $^{129}$Xe signal will drop because the sample does not have a chance to fully polarize.

A significant feature of this discovery is that substantially larger amounts of hyperpolarized xenon can be can now be produced according to this method than were possible using substantially pure xenon as a target gas. That is, the yield of hyperpolarized xenon as a function of time is substantially increased, notwithstanding the fact that the xenon is present as only a small fraction of the target gas.

Once the flowing target gas is hyperpolarized, the entire gas stream ($^{129}$Xe, $^4$He, and $N_2$) can be flowed through an accumulator according to the invention. The accumulator includes a cryostat, preferably operating in the temperature range of from about 4.2 K to about 157 K. A temperature of about 77 K is preferred due its convenience, i.e., about the temperature of liquid nitrogen (b.p.=77 K) which is a readily available refrigerant. However, lower temperatures are generally preferred, since longer polarization lifetimes can be obtained as the temperature of accumulation and storage are decreased. Accordingly, liquid helium (b.p.=4.2 K) would be an excellent refrigerant for storage of hyperpolarized $^{129}$Xe, since such an extraordinarily low temperature is theoretically capable of extending the spin-lattice relaxation time of $^{129}$Xe to about 2900 hr. Closed-cycle refrigeration units may also be employed.

In any event, polarized $^{129}$Xe passing through the cryostat immediately freezes due to its melting point being 157 K. If liquid-nitrogen cooling is used, only the hyperpolarized $^{129}$Xe will condense from the gas stream, since any quenching nitrogen gas will have a partial pressure of much less than one atmosphere, the condensation pressure for liquid nitrogen. Condensation of the nitrogen at colder accumulation temperatures will probably do no harm, but it can be completely avoided if needed by replacing the nitrogen quenching gas ($N_2$) by hydrogen ($H_2$). The bulk of the gas, i.e., the helium, simply passes through the cryostat and out through the exit port. Hence, a useful feature of this method is that it can be used to effectively separate (purify) the hyperpolarized xenon from the other, unwanted, components of the target gas mixture. Accordingly, a preferred property of the buffer gas is that it should be substantially separable from the xenon in this fashion.

Because the relaxation time $T_1$ of frozen $^{129}$Xe is significantly longer when maintained in an applied magnetic field, the cryostatic accumulator is preferably fitted with a small permanent magnet capable of such magnetic-field strengths in order to improve holding times. The primary consideration in choosing the strength of the applied field is that the field should enable accumulation and/or storage for a period of about the maximum possible spin-lattice relaxation time at the accumulation/storage temperature. Accordingly, the applied field should be at least about 500 G (0.05 T) at liquid nitrogen temperatures. We observe, however, that the selection of field strength is dependent upon the temperature at which the $^{129}$Xe is being accumulated or stored. Specifically, lower temperature accumulation and/or storage benefits from the use of higher field strength.

The accumulator manifold is preferably fitted with a pumping port so that it can be evacuated before use to eliminate any paramagnetic contaminants, such as oxygen. In addition, the interior surfaces of the manifold are preferably appropriately coated or otherwise treated (e.g., as described elsewhere herein for the polarization chamber, etc.) so that they are at least substantially non-depolarizing to the $^{129}$Xe.

The entrance port of the accumulator is preferably adapted to be placed in fluid communication with a polarization chamber in which the laser optical pumping and spin exchange take place. Thus, highly polarized $^{129}$Xe can be flowed from the pumping chamber through the entrance port of the accumulator. A valve allows the flow to be controlled as desired. The polarization chamber and accumulator reservoir may be manufactured as a single unit. Alternatively, a severable connection between the accumulator and the polarization chamber may be included, to permit removal and replacement of the accumulator reservoir.

As the polarization process proceeds, a significant mass of polarized $^{129}$Xe will form in the storage reservoir. Once the desired amount of xenon ice has been accumulated, the reservoir can be evacuated and optionally removed from the accumulator for various purposes. For example, a transportable reservoir can be removed to a longer-term storage apparatus, thereby freeing the accumulator to receive another reservoir for continued accumulation of hyperpolarized $^{129}$Xe. Upon removal from the accumulator or the longer-term storage, the filled reservoir can be used in situ or transported to an alternative site of use.

At any desired time, the reservoir containing the stored hyperpolarized xenon can be heated (passively or actively) to room temperature, to cause the polarized solid to thaw (sublime) to form a high pressure gas. Thus, the accumulator apparatus itself may include heating means. Alternatively, a remote storage or delivery device may include such heating means. If heat is actively applied, care should be taken to avoid imposing magnetic-field gradients on the hyperpolarized sample which might cause premature relaxation. The polarized high-pressure gas can then be harvested by opening a valve on the exit port of the storage chamber. A pressure release valve (e.g., 50 psi) on the outlet manifold can serve to prevent explosive release and thereby prevent possible injury to persons or property.

The apparatus described herein is capable of integration with MRI imaging systems consistent with the systems useful for imaging by means of hyperpolarized noble gases described in U.S. Pat. No. 5,543,396, the disclosure of which is incorporated herein by reference. Typical of such systems is a commercially available MR imaging unit including a 2-Tesla, 30-cm horizontal Omega CSI magnet (G.E. NMR Instruments, Fremont, Calif.) and associated apparatus, described in greater detail in Middleton et al., *Magn. Reson. in Med.* 33:271–275 (1995). The ability to produce large quantities of hyperpolarized noble gas can now be employed beneficially to permit the accumulation and storage of sufficient gas prior to imaging that no additional hyperpolarizing need be undertaken during the imaging itself. Thus, one or more subjects can now be imaged in a clinical setting using a single source of previously accumulated xenon. Alternatively, imaging can now be undertaken in which a continuous hyperpolarization procedure generates a continuing source of hyperpolarized gas supplied to a subject for study of respiration or other physiological processes enabled by the extraordinary properties of the noble gases. Previously, imaging of this sort was either impossible or extremely impractical due to the small amounts of hyperpolarized gases available for use.

The following examples are provided to assist in a further understanding of the invention. The particular materials and conditions employed are intended to be further illustrative of the invention and are not limiting upon the reasonable scope thereof.

EXAMPLE 1

A continuous flow polarization apparatus has been constructed generally in accordance with the structure illustrated in FIG. 1, described above. The pumping chamber is a glass cylinder 6 cm long and having a volume of about 30 cm$^3$. The optical axis is collinear with the longitudinal axis of the chamber.

We have found that the optimal flow through the pumping chamber is dependent upon temperature. For the hyperpolarization of $^{129}$Xe (3% in 96% $^4$He; 10 atm) in this 30 cm$^3$ chamber, the flow rate can be in the range of from about 300 cm$^3$/min to about 600 cm$^3$/min at 150° C. Modeling indicates that from about 20% to about 30% of the laser light is absorbed at 150° C., corresponding to a spin exchange time ($\tau_{SE}$) of 22 s, and an average rubidium polarization of about 50%.

EXAMPLE 2

The relaxation time of polarized solid $^{129}$Xe determines the timescale for accumulation. Accumulation times that are significantly longer than the solid $^{129}$Xe relaxation times will result in decreased $^{129}$Xe polarizations. At 77 K and a field of 500 G or more, $T_1 \approx 3$ hr. As noted above, for a pump chamber temperature of 150° C. the spin exchange time is $\tau_{SE}$=22 s. The saturation polarization of [Xe]=2 amagat in [He]=10 amagat is 88%. Setting the flow rate such that a given $^{129}$Xe spends a time $2\tau_{SE}$ in the pump chamber, the resulting $^{129}$Xe polarization is 86% of that, or P=76%. The corresponding xenon flow rate is F=(0.2 amagat×20 cm$^3$/44 s)=0.09 amagat cm$^3$ s$^{-1}$. Accumulating for 3 hr yields about 1 L of polarized gas at standard temperature and pressure (STP). Taking into account the relaxation of the solid, the resulting 1 L retains 63% of the initial polarization upon freezing, P=48%.

EXAMPLE 3

A gas mixture of 3% Xe having a natural isotopic composition of about 26% $^{129}$Xe, 1% N$_2$, and 96% $^4$He was polarized using the apparatus described in Example 1. In addition, an accumulator according to the invention was used to accumulate the gas leaving the pumping chamber. The accumulator used liquid nitrogen as a refrigerant for the accumulator reservoir. The reservoir was a glass cold finger through which the gas containing the hyperpolarized $^{129}$Xe flowed. A small permanent magnet producing a field of about 1800 G was installed to provide a suitable field to the reservoir. Glass conduits were used to convey the gas from the pumping chamber to the accumulator reservoir.

Using this system, 120 cm$^3$ (at STP) of hyperpolarized $^{129}$Xe was accumulated in 0.5 hr. The nominal flow rate of the target gas during accumulation was 80–100 cm$^3$/min at STP. Since the gas mixture was only 3% Xe, this permitted a xenon accumulation rate of up to about 3 cm$^3$/min at STP. Upon subliming, the $^{129}$Xe was allowed to expand back into the pumping chamber, which was equipped with a pulsed NMR coil. The NMR signal strength was determined to be about ¼ of the largest saturation even seen from the He:Xe:N$_2$ gas mixture in a sealed pump chamber. From computer modeling, it is believed that the saturation polarization of $^{129}$Xe during an optical pumping procedure is about 75%. The pressure of the sublimed xenon was measured with a capacitance manometer to be 1.21 atm compared to 0.27 atm of xenon in the gas mixture during pumping. Given the ratio of pressures and NMR signals, we arrived at a rough polarization of the accumulated $^{129}$Xe of 5%.

The net polarization obtained in this experiment was within an order of magnitude of the theoretical maximum polarization. Thus, while it must be recognized that this procedure was not optimized, it is shown that the continuous production of hyperpolarized $^{129}$Xe is possible using the method and apparatus of the invention. Moreover, the production and accumulation process preserved a significant amount of the polarization of the xenon. Based on this study, we expect improvements in yield for the sublimed gas.

Clearly, the volumes of hyperpolarized $^{129}$Xe obtained using the apparatus of the invention permit the generation of volumes of hyperpolarized noble gases on the order of at least liters per day. Accordingly, the invention now enables, for the first time, the production of sufficient polarized noble gases to enable clinical ventilation studies of human lung by MRI.

EXAMPLE 4

The volumes of the outlet manifold components in a constructed apparatus have been crudely calibrated (~±5%). The flow rate on the flow meter has been similarly calibrated, and appears accurate. The amount of xenon accumulated in the accumulator reservoir corresponds within errors to the flow rate read from the flow gauge during accumulation multiplied by the accumulation time. This indicates that substantially all of the xenon in the gas mixture is being effectively trapped in the accumulator.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method for accumulating hyperpolarized $^{129}$Xe, comprising:

flowing a source gas, comprising hyperpolarized $^{129}$Xe, through an accumulation reservoir adapted to permit gas flow therethrough, wherein said accumulation reservoir is refrigerated to a temperature which causes xenon to condense to frozen form and wherein a magnetic field is applied to said accumulation reservoir, and accumulating from said flowing source gas said hyperpolarized $^{129}$Xe in frozen form within said accumulation reservoir.

2. A method according to claim 1, wherein said accumulating is performed in an applied magnetic field which maximizes the spin-lattice relaxation time of said hyperpolarized $^{129}$Xe at the accumulation temperature.

3. A method according to claim 1, wherein said accumulating is performed for a period of up about the maximum possible spin-lattice relaxation time of $^{129}$Xe at the temperature at which the $^{129}$Xe is accumulated.

4. A method according to claim 1, wherein said source gas further comprises a quenching gas.

5. A method according to claim 4, wherein said quenching gas is selected from the group consisting of nitrogen and hydrogen.

6. A method according to claim 5, wherein said buffer gas is helium.

7. A method according to claim 1, wherein said source gas further comprises a buffer gas.

8. A method according to claim 1, wherein said source gas comprises from about 0.1% to about 5% hyperpolarized $^{129}$Xe, from about 0.1% to about 30% of said quenching gas, and the balance helium.

9. A method according to claim 8, wherein said source gas comprises about 1% hyperpolarized $^{129}$Xe, about 1% nitrogen, and about 98% helium.

10. A method according to claim 1, wherein said accumulating comprises selectively accumulating said hyperpolarized $^{129}$Xe at a temperature which prevents substantial condensation of other gases present in said flowing source gas.

11. A method according to claim 1, wherein said accumulation reservoir is refrigerated using a refrigerating fluid selected from the group consisting of liquid nitrogen, liquid hydrogen, and other liquefied gases.

12. A method according to claim 1, wherein said accumulation reservoir is refrigerated using a closed cycle refrigeration system.

13. A method according to claim 1, wherein said method further comprises hyperpolarizing $^{129}$Xe in said source gas to provide said hyperpolarized $^{129}$Xe.

14. A method according to claim 13, wherein said hyperpolarizing comprises hyperpolarizing said $^{129}$Xe by spin exchange with an alkali metal.

15. A method according to claim 13, wherein said hyperpolarizing provides a continuous flow of said source gas comprising hyperpolarized $^{129}$Xe, and wherein said accumulating of said hyperpolarized $^{129}$Xe is continued for a period of up to about the maximum possible spin-lattice relaxation time for the $^{129}$Xe at the temperature of the accumulation means.

16. A method according to claim 1, further comprising storing said accumulated hyperpolarized $^{129}$Xe at a temperature of about or below the freezing point of xenon.

17. A method according to claim 16, wherein said storing comprises storing said accumulated hyperpolarized $^{129}$Xe at a location remote from where said accumulating is performed.

18. A method according to claim 16, wherein said storing comprises storing said accumulated hyperpolarized $^{129}$Xe in an applied magnetic field which maximizes the spin-lattice relaxation time of said hyperpolarized $^{129}$Xe at the storage temperature.

19. Accumulator apparatus for continuous accumulation of hyperpolarized $^{129}$Xe, comprising:

a) an accumulation reservoir for accumulating hyperpolarized $^{129}$Xe from a source gas flowing therethrough said accumulation reservoir comprising an inlet and an outlet to permit gas flowthrough, b) refrigeration means for refrigerating said accumulation reservoir to a temperature which causes condensation and accumulation of said hyperpolarized $^{129}$Xe in frozen form within said accumulation reservoir, and c) magnetization means for applying a magnetic field to said accumulation reservoir.

20. Apparatus according to claim 19, wherein said magnetization means comprises means for applying a magnetic field to said accumulation reservoir which maximizes the spin-lattice relaxation time of said hyperpolarized $^{129}$Xe at the accumulation temperature.

21. Apparatus according to claim 19, wherein said refrigeration means comprises means for refrigerating said accumulation reservoir by means of a refrigerating fluid selected from the group consisting of liquid nitrogen, liquid helium, and other liquefied gases.

22. Apparatus according to claim 19, wherein said refrigeration means comprises a closed-cycle refrigeration system.

23. Apparatus according to claim 19, further comprising means for providing flowing hyperpolarized $^{129}$Xe to said accumulation reservoir.

24. Apparatus according to claim 23, wherein said providing means comprises hyperpolarization means for hyperpolarizing flowing $^{129}$Xe.

25. Apparatus according to claim 24, wherein said hyperpolarization means comprises:

a) a polarization chamber for polarizing said flowing $^{129}$Xe; and b) a light source capable of delivering hyperpolarizing radiation into said polarization chamber.

26. Apparatus according to claim 25, wherein said polarization chamber contains an alkali metal for providing an alkali-metal vapor during hyperpolarizing.

27. Apparatus according to claim 25, wherein said light source is capable of delivering hyperpolarizing radiation in an amount which induces hyperpolarizing of said $^{129}$Xe by spin exchange with an alkali metal.

28. Apparatus according to claim 24, wherein said accumulation reservoir is adapted to replaceably engage and operate with said hyperpolarization means and said refrigeration means.

29. Apparatus according to claim 19, wherein said accumulation reservoir is adapted to replaceably engage and operate with said refrigeration means.

30. Apparatus according to claim 19, wherein said inlet and said outlet of said accumulation reservoir further comprise sealable valves to control gas flow through said reservoir.

31. Apparatus according to claim 19, wherein said apparatus further comprises means for subliming said accumulated hyperpolarized $^{129}$Xe to provide xenon gas comprising hyperpolarized $^{129}$Xe.

32. Apparatus according to claim 19, wherein said refrigeration means comprises means for refrigerating said accumulation reservoir to a temperature of from about 4.2K to about 157K.

33. Apparatus according to claim 19, wherein an interior surface of said accumulation reservoir is treated to reduce depolarization of said hyperpolarized $^{129}$Xe.

34. A method for providing a. gas comprising hyperpolarized $^{129}$Xe, comprising:

a) providing a target gas comprising $^{129}$Xe and at least one other gas;

b) flowing said target gas through hyperpolarization means;

c) hyperpolarizing said $^{129}$Xe in said hyperpolarization means by spin exchange with an alkali metal to provide hyperpolarized $^{129}$Xe in said target gas;

d) flowing said target gas through an accumulation reservoir which is refrigerated to a temperature which causes xenon to condense in frozen form and to which a magnetic field is applied, to accumulate frozen hyperpolarized $^{129}$Xe within said accumulation reservoir while preventing substantial condensation of said at least one other gas of said flowing target gas;

e) thawing said frozen hyperpolarized $^{129}$Xe to provide a gas consisting essentially of xenon and comprising hyperpolarized $^{129}$Xe;

f) delivering said gas from said accumulation reservoir to provide a supply of said hyperpolarized $^{129}$Xe.

35. Apparatus for the accumulation and storage of hyperpolarized $^{129}$Xe in frozen form, comprising;

a replaceable accumulation reservoir having an inlet and an outlet to permit continuous gas flow therethrough, wherein said replaceable accumulation reservoir includes means to detachably engage and operate with hyperpolarization apparatus for producing flowing hyperpolarized $^{129}$Xe and delivering said flowing hyperpolarized $^{129}$Xe into said accumulation reservoir and wherein said apparatus further comprises integrated refrigeration means for refrigerating said accumulation reservoir to a temperature which causes xenon to condense to frozen form for maintaining said hyperpolarized $^{129}$Xe in frozen form.

36. Apparatus according to claim 35, wherein said apparatus further comprises integrated magnetization means for applying a magnetic field to said accumulation reservoir.

37. Apparatus for the accumulation and storage of hyperpolarized $^{129}$Xe in frozen form, comprising:

a replaceable accumulation reservoir having an inlet and an outlet to permit continuous gas flow therethrough, wherein said replaceable accumulation reservoir includes means to detachably engage and operate with hyperpolarization apparatus for producing flowing hyperpolarized $^{129}$Xe and delivering said flowing hyperpolarized $^{129}$Xe into said accumulation reservoir, and wherein said apparatus farther comprises integrated magnetization means for applying a magnetic field to said accumulation reservoir.

38. Apparatus according to claim 37, wherein said apparatus further comprises integrated refrigeration means for refrigerating said accumulation reservoir to a temperature which causes xenon to condense to frozen form for maintaining said hyperpolarized $^{129}$Xe in frozen form.

39. Apparatus for continuous production of hyperpolarized $^{129}$Xe, comprising:

a) source gas delivery means adapted for providing flowing $^{129}$Xe, b) hyperpolarization means for hyperpolarizing said flowing $^{129}$Xe to provide flowing hyperpolarized $^{129}$Xe, and c) accumulation means for accumulating said hyperpolarized $^{129}$Xe, wherein said accumulation means comprises:

1) an accumulation reservoir for accumulating said hyperpolarized $^{129}$Xe, 2) refrigeration means for refrigerating said accumulation reservoir to a temperature which causes said hyperpolarized $^{129}$Xe to condense and to accumulate in said accumulation reservoir in frozen form, and 3) magnetization means for applying a magnetic field to said accumulation reservoir.

40. A method for continuous accumulation of a hyperpolarized $^{129}$Xe, comprising:

flowing a target gas comprising hyperpolarized $^{129}$Xe through accumulator means to accumulate said hyperpolarized $^{129}$Xe, wherein said accumulator means comprises:

a) an accumulation reservoir for accumulating hyperpolarized $^{129}$Xe;

b) refrigeration means for refrigerating said accumulation reservoir to a temperature which causes said hyperpolarized $^{129}$Xe to condense and to accumulate in said accumulation reservoir in frozen form, and c) magnetization means for applying a magnetic field to said accumulation reservoir.

41. A method for continuous accumulation of hyperpolarized $^{129}$Xe, comprising:

a) flowing a target gas comprising $^{129}$Xe through hyperpolarization means, b) hyperpolarizing said $^{129}$Xe by means of spin exchange with an alkali metal in said hyperpolarization means to provide hyperpolarized $^{129}$Xe in said target gas, and c) flowing said target gas through accumulator means to accumulate hyperpolarized $^{129}$Xe in frozen form;

wherein said accumulator means comprises:

1) an accumulation reservoir for accumulating said frozen hyperpolarized $^{129}$Xe;

2) refrigeration means for refrigerating said accumulation reservoir to a temperature which causes said hyperpolarized $^{129}$Xe to condense and to accumulate in said accumulation reservoir in frozen form, and 3) magnetization means for applying a magnetic field to said accumulation reservoir.

* * * * *

UNITED STATES PATENT AND TRADEMARK OFFICE
CERTIFICATE OF CORRECTION

PATENT NO. : 5,809,801
DATED : September 22, 1998
INVENTOR(S) : Gordon D. Cates, Jr., Bastiaan Driehuys, William Happer, Eli Miron, Brian Saam and Daniel Walter It is certified that error appears in the above-identified patent and that said Letters Patent is hereby corrected as shown below:

On the title page, Item [75] Inventor(s), insert --

The following inventor's name was omitted from the list of inventors on the patent.
Please add the following after Brian Saam, Princeton, N.J.:
   Daniel Walter, Chicago, IL --.

Signed and Sealed this

Fourth Day of May, 1999

Q. TODD DICKINSON

Attest:

Attesting Officer

Acting Commissioner of Patents and Trademarks